United States Patent [19]
Yoshida et al.

[11] Patent Number: 4,536,577
[45] Date of Patent: Aug. 20, 1985

[54] PROCESS FOR PREPARING 2-ALKYL-4-AMINO-5-AMINOMETHYL-PYRIMIDINE

[75] Inventors: Hiroshi Yoshida; Sadao Niida, both of Ube, Japan

[73] Assignee: Ube Industries, Ltd., Ube, Japan

[21] Appl. No.: 593,631

[22] Filed: Mar. 26, 1984

[30] Foreign Application Priority Data

Apr. 7, 1983 [JP] Japan ................... 58-59960

[51] Int. Cl.$^3$ ............................. C07D 239/02
[52] U.S. Cl. ................... 544/326; 564/397; 564/398; 564/472; 564/473
[58] Field of Search ............... 544/326; 564/397, 398, 564/472, 473

[56] References Cited
U.S. PATENT DOCUMENTS 3,223,734 12/1965 Fallstad et al. .............. 564/480
4,210,605 7/1980 Hoshino et al. ............. 564/473

OTHER PUBLICATIONS

Winans, JACS 61, 3566, (1939).
Synthetic Organic Chem. by Wagner et al, 1953, pp. 662, 663, 656.
March, Advanced Org. Chem., 2nd Edition, 1977, p. 819.

Primary Examiner—Donald G. Daus
Assistant Examiner—Cecilia Shen
Attorney, Agent, or Firm—Frishauf, Holtz, Goodman & Woodward

[57] ABSTRACT

Disclosed is a process for preparing 2-alkyl-4-amino-5-aminomethylpyrimidine comprising (i) a first step of reacting 2-alkyl-4-amino-5-formylpyrimidine with ammonia in an inert solvent in the presence of at least one compound selected from heteropolyacids, isopolyacids, oxyacids and salts thereof containing molybdenum or tungsten, and (ii) a second step of reacting the reaction product in the first step catalytically with ammonia and hydrogen in an inert solvent in the presence of a reducing catalyst together with or without a hydroxide of an alkali metal or alkaline earth metal.

16 Claims, No Drawings

PROCESS FOR PREPARING 2-ALKYL-4-AMINO-5-AMINOMETHYLPYRIMIDINE

BACKGROUND OF THE INVENTION

This invention relates to a process for preparing a 2-alkyl-4-amino-5-aminomethylpyrimidine. More particularly, it relates to an improved process for preparing 2-alkyl-4-amino-5-aminomethylpyrimidine by reductive amination of a 2-alkyl-4-amino-5-formylpyrimidine with ammonia and hydrogen.

It is known that 2-alkyl-4-amino-5-aminomethylpyrimidine is an important intermediate compound for synthesis of vitamin $B_1$ and its analogous compounds.

In general, it has been known in the art to produce a primary amine such as 2-alkyl-4-amino-5-aminomethylpyrimidine by reductive amination of an aldehyde such as 2-alkyl-4-amino-5-formylpyrimidine with ammonia and hydrogen. The reaction routes are considered to be represented by the following reaction scheme:

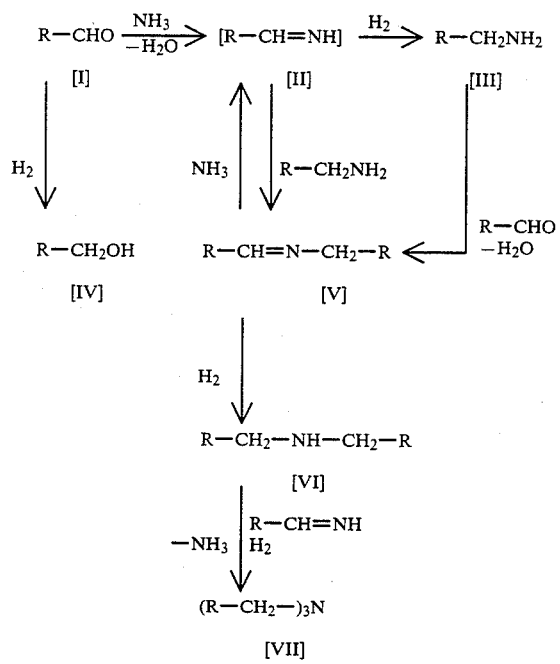

As can be seen from said reaction routes, it has been estimated that an aldehyde [I] is first iminated to form an aldimine [II] as the intermediate, followed by hydrogen reduction, to give a desired primary amine [III] such as 2-alkyl-4-amino-5-aminomethylpyrimidine.

In the prior art, said reaction has been practiced by dissolving an aldehyde of the starting material in an inert solvent and blowing simultaneously ammonia and hydrogen into the solution in the presence of a reducing catalyst, as disclosed in Japanese Unexamined Patent Publication. (KOKAI) No. 140079/1983, thereby producing resultant products in an yield of from about 80 to 90%. However, other than the desired primary amine, a number of by-products, primary alcohols, secondary and tertiary amines represented by the above [IV] to [VII] such as 2-alkyl-4-amino-5-hydroxymethylpyrimidine and di-(2-alkyl-4-amino-5-pyrimidylmethyl)amine are formed in large amounts, whereby the yield and the selectivity of the primary amine such as 2-alkyl-4-amino-5-aminomethylpyrimidine are very low. As a measure to cope with this problem, there has been only a proposal to control the amount of ammonia relative to the aldehyde of the starting material.

For example, according to JACS 61 3566 (1939), in the case of an aldehyde having no active hydrogen on α-carbon such as benzaldehyde, a primary amine is disclosed to be formed preferentially in an alcoholic solution of ammonia by controlling the molar ratio of the aldehyde to ammonia. However, even in the process according to this proposal, the yield of the primary amine is 80 to 90%, with the secondary amine being by-produced at a yield of 6 to 16%.

SUMMARY OF THE INVENTION

The present inventors have made extensive studies with an aim to develop a process capable of preparing a primary amine, in particular, 2-alkyl-4-amino-5-aminomethylpyrimidine, at a high yield and a high selectivity by reductive amination of 2-alkyl-4-amino-5-formylpyrimidine. As a result, it has been found that, in place of direct reductive amination of 2-alkyl-4-amino-5-formylpyrimidine with ammonia and hydrogen, 2-alkyl-4-amino-5-formylpyrimidine may be previously allowed to react with ammonia in an inert solvent in the presence of a specific compound to synthesize an aldimine compound as the intermediate at a good yield, followed by the catalytic reaction of said intermediate with ammonia and hydrogen in the presence of a reducing catalyst with or without a hydroxide of an alkali metal or alkaline earth metal, whereby formation of the aforesaid by-products can be suppressed to give very high yield and selectivity of the desired product to accomplish the present invention.

Thus, this invention is to provide, as one embodiment of the invention, an industrially advantageous process for preparing 2-alkyl-4-amino-5-aminomethylpyrimidine comprising;

(i) a first step of reacting 2-alkyl-4-amino-5-formylpyrimidine with ammonia in an inert solvent in the presence of at least one compound selected from heteropolyacids, isopolyacids, oxyacids (oxygen acids) and salts thereof containing molybdenum or tungsten, and (ii) a second step of reacting the reaction product in the first step catalytically with ammonia and hydrogen in an inert solvent in the presence of a reducing catalyst.

In another embodiment of this invention, the above reducing catalyst to be used in the second step may be present in the reaction system together with a hydroxide of an alkali metal or alkaline earth metal.

DESCRIPTION OF THE PREFERRED EMBODIMENTS

This invention is now described in detail below.

(1) First step:

The starting material 2-alkyl-4-amino-5-formylpyrimidine has a structure represented by the following general formula:

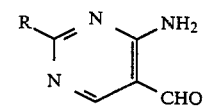

wherein R may represent a lower alkyl group such as methyl, ethyl, propyl and butyl.

This starting material can be readily synthesized by, for example, hydrolysis of 2-alkyl-4-amino-5-dialkoxymethylpyrimidine in the presence of an acid. The starting 2-alkyl-4-amino-5-formylpyrimidine may be provided for use also as mineral acid salts such as of sulfuric acid, nitric acid, hydrochloric acid, etc.

In this first step, 2-alkyl-4-amino-5-formylpyrimidine is reacted with ammonia in an inert solvent in the presence of at least one compound selected from heteropolyacids, isopolyacids, oxyacids (oxygen acids) and salts thereof containing molybdenum or tungsten.

The heteropolyacid, isopolyacid, oxyacid and salts thereof containing molybdenum or tungsten to be provided for use in this step may include heteropolyacids such as phosphomolybdic acid, phosphotungstic acid, silicomolybdic acid, phosphomolybdotungstic acid, phosphovanadomolybdic acid, silicovanadotungstic acid and the like; oxy acids selected from molybdic acid and tungstic acid; and isopolyacids which are condensed acids of said oxyacids; and further alkali metal salts such as of sodium or potassium or ammonium salts of these various acids. Its amount may be preferably 0.001 to 5 wt. % based on the starting 2-alkyl-4-amino-5-formylpyrimidine. With an amount less than the lower limit value, the reaction will proceed slowly, while an amount in excess of the upper limit value is not economical, although formation of an aldimine of the intermediate will not be badly affected thereby.

As the inert solvent, it is preferred to use a lower aliphatic alcohol such as methanol, ethanol, propanol and butanol, but mixtures of a lower aliphatic alcohol with an ether such as dioxane, tetrahydrofuran or diethylether or with a hydrocarbon such as benzene, toluene, xylene, hexane or cyclohexane are also useful. These solvents may be used in an amount, which may differ depending on the starting 2-alkyl-4-amino-5-formylpyrimidine and the aldimine formed, but it is generally preferred to use 3 to 50 parts by weight, more preferably 3 to 30 parts by weight, per one part by weight of the starting 2-alkyl-4-amino-5-formylpyrimidine.

As ammonia, liquid ammonia, ammonia gas, or an ammonia solution may be provided for use, and its amount may be one mole or more, preferably 4 to 500 moles or most preferably 4 to 200 moles, per mole of the starting 2-alkyl-4-amino-5-formylpyrimidine.

The reaction is carried out generally under normal pressure at a temperature of 0° to 130° C., preferably of room temperature to 110° C., for 0.5 to 24 hours, preferably for 0.5 to 10 hours.

By this reaction, it is presumed that the starting 2-alkyl-4-amino-5-formylpyrimidine has been converted to an aldimine represented by the following general formula:

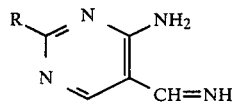

(wherein R have the same meaning as in the foregoing).

(2) Second step:

The aldimine which is the reaction product in the first step is brought into contact with ammonia and hydrogen in an inert solvent in the presence of a reducing catalyst with or without a hydroxide of an alkali metal or alkaline earth metal.

The inert solvent in this step may be the same as used in the first step, and its amount may preferably be 3 to 50 parts by weight, more preferably 3 to 30 parts by weight, per 1 part by weight of the starting 2-alkyl-4-amino-5-formylpyrimidine.

Thus, in this step, the same kind of the inert solvent as used in the first step is available, and the compounds used in the first step such as heteropolyacid have no deleterious effect on the reaction in this step. Accordingly, the catalytic reaction in the second step can be carried out without isolation of the reaction product from the solution in the first step after the reaction by adding a reducing catalyst together with or without a hydroxide of an alkali metal or alkaline earth metal into the solution and introducing ammonia and hydrogen thereinto, after optionally supplementing the inert solvent or removing ammonia insoluble to the inert solvent. Alternatively, it is also possible to prepare previously a solution in which a reducing catalyst together with or without a hydroxide of an alkali metal or alkaline earth metal, ammonia and hydrogen are added in an inert solvent, and the reaction mixture in the first step may be added at one time or gradually over 0.5 to 10 hours. In these methods, when an excessive amount of ammonia is employed in the first step, it is not necessarily required to supplement ammonia in the second step.

Further, the catalytic reaction in this step can also be carried out by use of aldimine obtained by isolation from the solution after the reaction in the first step as the starting material, as a matter of course.

As the reducing catalyst to be employed, metals such as palladium, platinum, ruthenium, rhodium, nickel, cobalt, etc. are useful. Of these, particularly preferred are parradium and rhodium from a viewpoint of catalyst life. These metals are generally used under metallic states, but they can be also provided for use in the form of salts, oxides or alloys. Nickel or cobalt may also be prepared by development of Raney nickel or Raney cobalt in a conventional manner, respectively. These catalysts may be used either individually or also as a mixture of two or more catalysts. Further, these catalysts may also be supported on a carrier such as activated charcoal, alumina, silica, silicon carbide, diatomaceous earth, pumice, zeolite, molecular sieve, etc.

These catalysts may be used preferably in an amount of 0.0005 to 1 gram atom calculated as metal, based on one mole of the starting 2-alkyl-4-amino-5-formylpyrimidine.

These catalysts may in advance be heat-treated in a hydrogen gas. This advance treatment is carried out by bringing 1 g of the reducing catalyst into contact with hydrogen gas or hydrogen gas diluted with inert gas such as nitrogen and argon, at a flow rate of 50 to 2,000 ml/min, preferably 100 to 1,000 ml/min, for 1 to 10 hours while keeping the temperature at 50° to 500° C.

The hydroxide of an alkali metal or an alkaline earth metal to be used may include, for example, hydroxides of an alkali metal such as sodium hydroxide, potassium hydroxide and lithium hydroxide; hydroxides of an alkaline earth metal such as magnesium hydroxide, calcium hydroxide and barium hydroxide. Of these, sodium hydroxide and potassium hydroxide are preferred in particular. The hydroxide of an alkali metal or an alkaline earth metal may be directly used in a solid state, or may be used by dissolving it in water or in the above-mentioned inert solvent. Its amount may be 0.001 to 0.2 mole, preferably 0.01 to 0.1 mole, per mole of the starting 2-alkyl-4-amino-5-formylpyrimidine.

As ammonia, liquid ammonia, ammonia gas or an ammonia solution may be available similarly as in the first step. Its amount may be one mole or more, preferably 4 to 300 moles per one mole of the starting 2-alkyl-4-amino-5-formylpyrimidine.

It is possible to omit supplement of ammonia in the second step as described above when an excessive amount of ammonia has been used in the first step and 1 mole or more of the ammonia per mole of the starting 2-alkyl-4-amino-5-formylpyrimidine have remained in the system where the reaction in the first step has been completed and the second step catalytic reaction is subsequently conducted without isolation of the reaction product from the system after the reaction in the first step.

Hydrogen may be used in an amount of 1 mole or more, preferably 5 to 400 moles, per one mole of the starting 2-alkyl-4-amino-5-formylpyrimidine.

The reaction in this second step may preferably be conducted at a temperature ranging from 0° to 200° C., more preferably from room temperature to 120° C. The reaction can proceed even under normal pressure, but will proceed more rapidly under pressurization, and therefore it is preferred to carry out the reaction generally under a pressure of the hydrogen partial pressure of 1 to 100 Kg/cm² G. The reaction time may sufficiently be about 0.5 to 10 hours.

After completion of the reaction, for example, the reaction mixture may be cooled to remove insolubles such as the catalyst, and thereafter the resultant 2-alkyl-4-amino-5-aminomethylpyrimidine represented by the following general formula and corresponding to the starting 2-alkyl-4-amino-5-formylpyrimidine provided for use can be isolated and recovered in the free form or in the form of a mineral salt by a conventional method.

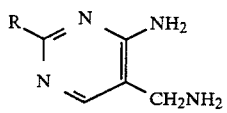

(wherein R have the same meaning as in the foregoing).

The present invention is further illustrated by the following Examples and Comparative examples, in which the yields of the products are all based on 2-alkyl-4-amino-5-formylpyrimidine provided for use.

EXAMPLE 1

Into an Erlenmeyer's flask of 100 ml, 2.00 g (14.6 millimole) of 2-methyl-4-amino-5-formylpyrimidine, 40 g of 20 wt. % ammonia-methanol solution and 0.20 g of 0.1 wt. % phosphomolybdic acid ($H_3Mo_{12}PO_{40}\cdot nH_2O$)-methanol solution were added, and the mixture was stirred overnight under room temperature, with the flask being closely stoppered. Then, the whole amount of the reaction mixture was charged into a stainless steel autoclave of an inner volume of 200 ml, followed by charging with 0.10 g of 5 wt. % Pd/C, 12 g of liquid ammonia and hydrogen gas of 50 Kg/cm² G and elevation of the temperature to 45° C. under stirring, whereat the reaction was carried out for one hour. After completion of the reaction, the mixture was cooled and unaltered reaction gases were released, followed by opening of the autoclave, and the catalyst was recovered by filtration. The washing obtained by washing the catalyst with methanol was combined with the filtrate and, after removal of ammonia by concentration under reduced pressure, the methanol solution was adjusted to pH of about 3 with 1 N-HCl and subjected to quantitative determination by liquid chromatography according to the internal reference method. As the result, the yield of 2-methyl-4-amino-5-aminomethylpyrimidine was found to be 95.3%.

COMPARATIVE EXAMPLE 1

An experiment was carried out according to the same procedure as in Example 1 except that no 0.1 wt. % phosphomolybdic acid-methanol solution was employed. As the result, the yield of 2-methyl-4-amino-5-aminomethylpyrimidine was found to be 55.3%.

EXAMPLE 2

An experiment was conducted according to the same procedure as in Example 1, except that 0.5 mg of phosphotungstic acid ($H_3W_{12}PO_{40}\cdot nH_2O$) was employed in place of the 0.1 wt. % phosphomolybdic acid-methanol solution. As the result, the yield of 2-methyl-4-amino-5-aminomethylpyrimidine was found to be 94.8%

EXAMPLE 3

An experiment was conducted according to the same procedure as in Example 1, except that the amount of 2-methyl-4-amino-5-formylpyrimidine was changed to 4.00 g (29.2 millimole) and the amount of the 0.1 wt. % phosphomolybdic acid ($H_3Mo_{12}PO_{40}\cdot nH_2O$)-methanol solution changed to 0.40 g and further the amount of the 5 wt. % Pd/C change to 0.20 g. As the result, the yield of 2-methyl-4-amino-5-aminomethylpyrimidine was found to be 93.0%.

EXAMPLE 4

Into an Erlenmeyer's flask of 100 ml, 2.00 g (14.6 millimole) of 2-methyl-4-amino-5-formylpyrimidine, 40 g of 20 wt. % ammonia-methanol solution and 2.0 mg of molybdic acid ($H_2MoO_4\cdot H_2O$) were added, and the mixture was stirred for 2 hours under room temperature, with the flask being closely stoppered. Following subsequently the same procedure as in Example 1, 2-methyl-4-amino-5-aminomethylpyrimidine was obtained at a yield of 93.5%.

EXAMPLE 5

An experiment was conducted according to the same procedure as in Example 4, except that 2.0 mg of ammonium molybdate [$(NH_4)_6Mo_7O_{24}\cdot 4H_2O$)] was used in place of molybdic acid. As the result, the yield of 2-methyl-4-amino-5-aminomethylpyrimidine was found to be 92.9%.

EXAMPLE 6

An experiment was conducted according to the same procedure as in Example 4, except that 2.0 mg of sodium phosphomolybdate ($Na_3Mo_{12}PO_{40}\cdot nH_2O$) was used in place of molybdic acid. As the result, the yield of 2-methyl-4-amino-5-aminomethylpyrimidine was found to be 96.1%.

EXAMPLE 7

Into an Erlenmeyer's flask of 100 ml, 2.00 g (14.6 millimole) of 2-methyl-4-amino-5-formylpyrimidine, 40 g of 20 wt. % ammonia-methanol solution and 0.20 g of 0.1 wt. % phosphomolybdic acid ($H_3Mo_{12}PO_{40}\cdot nH_2O$)-methanol solution were added, and the mixture was stirred overnight under room temperature, with the flask being closely stoppered. Then, the whole amount of the reaction mixture was charged into a stainless steel autoclave of an inner volume of 200 ml, followed by charging with 0.10 g of 5 wt. % Pd/C, 12 g of liquid ammonia, 1.6 g of 1 wt % sodium hydroxide—methanol solution and hydrogen gas of 50 Kg/cm² G and elevation of the temperature to 45° C. under stirring, whereat the reaction was carried out for one hour. After completion of the reaction, the mixture was cooled and unaltered reaction gases were released, followed by opening of the autoclave, and the catalyst was recovered by filtration. The washing obtained by washing the catalyst with methanol was combined with the filtrate and, after removal of ammonia by concentration under reduced pressure, the methanol solution was adjusted to pH of about 3 with 1 N-HCl and subjected to quantitative determination by liquid chromatography according to the internal reference method. Results were as follows:

Yield of 2-methyl-4-amino-5-aminomethylpyrimidine: 96.5%

Yield of 2-methyl-4-amino-5-hydroxymethylpyrimidine: 0.9%

Yield of di-(2-methyl-4-amino-5-pyrimidylmethyl)amine: 1.0%

EXAMPLE 8

An experiment was conducted according to the same procedures as in Example 7, except that 0.25 g of 5 wt. % Rh/C was used in place of the 5 wt. % Pd/C, to obtain results as follows:

Yield of 2-methyl-4-amino-5-aminomethylpyrimidine: 96.2%

Yield of 2-methyl-4-amino-5-hydroxymethylpyrimidine: 1.0%

Yield of di-(2-methyl-4-amino-5-pyrimidylmethyl)amine: 1.1%

EXAMPLE 9

An experiment was conducted according to the same procedures as in Example 7, except that 2.0 g (13.2 millimole) of 2-ethyl-4-amino-5-formylpyrimidine was used as the starting material in place of the 2-methyl-4-amino-5-formylpyrimidine used, and further that the temperature and time employed for the heat treatment of the 5 wt. % Pd/C under hydrogen gas flow was changed to 300° C. and one hour, respectively. Results were as follows.

Yield of 2-ethyl-4-amino-5-aminomethylpyrimidine: 96.6%

Yield of 2-ethyl-4-amino-5-hydroxymethylpyrimidine: 0.7%

Yield of di-(2-ethyl-4-amino-5-pyrimidylmethyl)amine: 1.4%.

We claim:
1. A process for preparing 2-alkyl-4-amino-5-aminomethylpyrimidine comprising;
  (i) a first step of reacting 2-alkyl-4-amino-5-formylpyrimidine with ammonia in an inert solvent in the presence of at least one compound selected from heteropolyacids, isopolyacids, oxyacids and salts thereof containing molybdenum or tungsten, and
  (ii) a second step of reacting the reaction product in the first step catalytically with ammonia and hydrogen in an inert solvent in the presence of a reducing catalyst.

2. The process according to claim 1, wherein said compound is selected from the group consisting of phosphomolybdic acid, phosphotungstic acid, silicomolybdic acid, phosphomolybdotungstic acid, phosphovanadomolybdic acid, silicovanadotungstic acid, molybdic acid, tungstic acid, isopolyacid of molybdic acid or tungstic acid and alkali metal salts or ammonium salts of these acids.

3. The process according to claim 1, wherein said compound is used in an amount of about 0.001 to 5 wt. % based on 2-alkyl-4-amino-5-formylpyrimidine.

4. The process according to claim 1, wherein said inert solvent is selected from the group consisting of methanol, ethanol, propanol, butanol, a mixture of these alcohols with dioxane, tetrahydrofuran, benzene, toluene, xylene, hexane or cyclohexane.

5. The process according to claim 1, wherein said inert solvent is used in an amount of about 3 to 50 parts by weight per one part by weight of 2-alkyl-4-amino-5-formylpyrimidine.

6. The process according to claim 1, wherein said ammonia is used in an amount of about 4 mole to 500 moles per mole of 2-alkyl-4-amino-5-formylpyrimidine.

7. The process according to claim 1, wherein the reaction in the first step is carried out under normal pressure at a temperature of about 0° to 130° C. for 0.5 to 24 hours.

8. The process according to claim 1, wherein said reducing catalyst is selected from the group consisting of palladium, platinum, ruthenium, rhodium, nickel, cobalt and, a salt, oxide or alloy of these metals.

9. The process according to claim 8, wherein said reducing catalyst is at least one of palladium and rhodium.

10. The process according to claim 1, wherein said reducing catalyst is used in an amount of about 0.0005 to 1 gram atom calculated as metal, based on one mole of 2-alkyl-4-amino-5-formylpyrimidine.

11. The process according to claim 1, wherein the reaction in the second step is carried out in the presence of said reducing catalyst and a hydroxide of an alkali metal or alkaline earth metal.

12. The process according to claim 11, wherein said hydroxide of an alkali metal or alkaline earth metal is selected from the group consisting of sodium hydroxide, potassium hydroxide and lithium hydroxide, magnesium hudroxide, calcium hydroxide and barium hydroxide.

13. The process according to claim 10, wherein said hydroxide of an alkali metal or alkaline earth metal is used in an amount of about 0.001 to 0.2 mole per mole of 2-alkyl-4-amino-5-formylpyrimidine.

14. The process according to claim 1, wherein said hydrogen is used in an amount of about 1 mole to 400 moles per one mole of 2-alkyl-4-amino-5-formylpyrimidine.

15. The process according to claim 1, wherein the reaction in the second step is carried out at a temperature ranging from about 0° to 200° C. for about 0.5 to 10 hours.

16. The process according to claim 15, wherein the reaction is carried out under a pressure of the hydrogen partial pressure of 1 to 100 Kg/cm² G.

* * * * *